(12) United States Patent
Zeien

(10) Patent No.: US 11,153,696 B2
(45) Date of Patent: Oct. 19, 2021

(54) EAR CANAL MODELING USING PATTERN PROJECTION

(71) Applicant: VIRTUAL 3-D TECHNOLOGIES CORP., Charlton, MA (US)

(72) Inventor: Robert Zeien, Charlton, MA (US)

(73) Assignee: VIRTUAL 3-D TECHNOLOGIES CORP., Charlton, MA (US)

( * ) Notice: Subject to any disclaimer, the term of this patent is extended or adjusted under 35 U.S.C. 154(b) by 202 days.

(21) Appl. No.: 15/894,567

(22) Filed: Feb. 12, 2018

(65) Prior Publication Data

US 2018/0234600 A1 Aug. 16, 2018

Related U.S. Application Data

(60) Provisional application No. 62/458,691, filed on Feb. 14, 2017.

(51) Int. Cl.
*H04R 25/00* (2006.01)
*H04N 5/225* (2006.01)
(Continued)

(52) U.S. Cl.
CPC ....... *H04R 25/652* (2013.01); *A61B 1/00009* (2013.01); *A61B 1/00179* (2013.01);
(Continued)

(58) Field of Classification Search
CPC ............ A61B 1/00009; A61B 1/00179; A61B 1/00193; A61B 1/05; A61B 1/0676;
(Continued)

(56) References Cited

U.S. PATENT DOCUMENTS

| 4,641,972 A | 2/1987 | Halioua et al. |
| 5,016,173 A | 5/1991 | Kenet et al. |

(Continued)

FOREIGN PATENT DOCUMENTS

| CN | 101264002 A | 9/2008 |
| CN | 101716077 A | 6/2010 |

(Continued)

OTHER PUBLICATIONS

Azim, S. (Lantos Technologies), "Making a Digital Impression Using 3D Ear Canal Scanning," hearingreview.com (2012).

(Continued)

*Primary Examiner* — Peter D Le
(74) *Attorney, Agent, or Firm* — Potomac Law Group, PLLC; Douglas E. Ringel

(57) ABSTRACT

Systems and methods are disclosed for making three-dimensional models of the inside of an ear canal using a projected pattern. A system comprises a probe adapted to be inserted into the ear canal. The probe comprises a narrow portion adapted to fit inside the ear canal and a wide portion adapted to be wider than the ear canal, which may be formed by a tapered stop. An illumination subsystem projects a pattern of light from the distal end of the probe onto a surface of the ear canal, the pattern being modulated by the three-dimensional surface of the ear canal. An imaging subsystem captures a series of individual images of the pattern of light projected onto the surface of the ear canal. A computer subsystem calculates digital three-dimensional representations from the individual images and stitches them together to generate a digital three-dimensional model of the ear canal.

16 Claims, 4 Drawing Sheets

(51) Int. Cl.

| | | |
|---|---|---|
| *G06T 7/521* | (2017.01) | |
| *A61B 1/227* | (2006.01) | |
| *G06T 3/40* | (2006.01) | |
| *G06T 17/00* | (2006.01) | |
| *A61B 5/00* | (2006.01) | |
| *A61B 5/107* | (2006.01) | |
| *A61B 1/00* | (2006.01) | |
| *G01B 11/25* | (2006.01) | |
| *A61B 1/05* | (2006.01) | |
| *A61B 1/06* | (2006.01) | |

(52) U.S. Cl.
CPC .......... *A61B 1/00193* (2013.01); *A61B 1/227* (2013.01); *A61B 5/004* (2013.01); *A61B 5/0082* (2013.01); *A61B 5/1077* (2013.01); *A61B 5/1079* (2013.01); *A61B 5/6817* (2013.01); *G01B 11/25* (2013.01); *G06T 3/4038* (2013.01); *G06T 7/521* (2017.01); *G06T 17/00* (2013.01); *H04N 5/2251* (2013.01); *H04N 5/2256* (2013.01); *A61B 1/05* (2013.01); *A61B 1/0676* (2013.01); *H04N 2005/2255* (2013.01); *H04R 2225/77* (2013.01)

(58) Field of Classification Search
CPC ....... A61B 1/227; A61B 5/004; A61B 5/0082; A61B 5/1077; A61B 5/1079; A61B 5/6817; G01B 11/25; G06T 17/00; G06T 3/4038; G06T 7/521; H04N 2005/2255; H04N 5/2251; H04N 5/2256; H04R 2225/77; H04R 25/652
See application file for complete search history.

(56) References Cited

U.S. PATENT DOCUMENTS

| | | | |
|---|---|---|---|
| 5,363,839 A * | 11/1994 | Lankford | A61B 1/04 600/112 |
| 5,487,012 A * | 1/1996 | Topholm | G05B 19/4207 700/163 |
| 5,581,352 A | 12/1996 | Zeien | |
| 5,587,832 A | 12/1996 | Krause | |
| 5,615,003 A | 3/1997 | Hermary et al. | |
| 5,784,098 A | 7/1998 | Shoji et al. | |
| 5,847,832 A * | 12/1998 | Liskow | A61B 5/0064 356/613 |
| 6,084,712 A | 7/2000 | Harding | |
| 6,115,058 A | 9/2000 | Omori et al. | |
| 6,134,003 A | 10/2000 | Tearney et al. | |
| 6,178,346 B1 | 1/2001 | Amundson et al. | |
| 6,332,087 B1 | 12/2001 | Svenson et al. | |
| 6,364,831 B1 | 4/2002 | Crowley | |
| 6,475,138 B1 * | 11/2002 | Schechter | A61B 18/20 600/108 |
| 6,503,195 B1 | 1/2003 | Keller et al. | |
| 6,579,285 B2 | 6/2003 | Sinofsky | |
| 6,695,779 B2 | 2/2004 | Sauer et al. | |
| 6,832,984 B2 | 12/2004 | Stelzer et al. | |
| 7,153,299 B1 | 12/2006 | Tu et al. | |
| 7,385,708 B2 | 6/2008 | Ackerman et al. | |
| 7,492,398 B1 | 2/2009 | Norita et al. | |
| 7,728,868 B2 | 6/2010 | Razzaque et al. | |
| 7,734,061 B2 | 6/2010 | Breed et al. | |
| 7,742,232 B2 | 6/2010 | Cho et al. | |
| 7,747,067 B2 | 6/2010 | Popescu et al. | |
| 7,751,694 B2 | 7/2010 | Cho et al. | |
| 7,812,968 B2 | 10/2010 | Bendall et al. | |
| 7,821,649 B2 | 10/2010 | Bendall et al. | |
| 7,846,107 B2 | 12/2010 | Hoffman et al. | |
| 8,094,322 B2 | 1/2012 | Mayer et al. | |
| 8,105,233 B2 | 1/2012 | Abou El Kheir | |
| 8,123,722 B2 | 2/2012 | Chang et al. | |
| 8,235,985 B2 | 8/2012 | Saadat et al. | |
| 8,419,613 B2 | 4/2013 | Saadat et al. | |
| 8,422,030 B2 | 4/2013 | Bendall et al. | |
| 8,900,219 B2 | 12/2014 | Sinofsky et al. | |
| 9,254,103 B2 | 2/2016 | Krishnaswamy et al. | |
| 9,326,668 B1 * | 5/2016 | Berbee | A61B 1/227 |
| 9,456,752 B2 | 10/2016 | Zeien | |
| 9,867,528 B1 * | 1/2018 | Boppart | A61B 1/2275 |
| 2003/0164952 A1 | 9/2003 | Deichmann et al. | |
| 2003/0174208 A1 | 9/2003 | Glukhovsky et al. | |
| 2004/0133085 A1 | 7/2004 | Hall | |
| 2004/0254474 A1 | 12/2004 | Seibel et al. | |
| 2005/0088435 A1 * | 4/2005 | Geng | G06T 17/10 345/419 |
| 2005/0168735 A1 | 8/2005 | Boppart et al. | |
| 2005/0182295 A1 | 8/2005 | Soper et al. | |
| 2005/0219552 A1 | 10/2005 | Ackerman et al. | |
| 2006/0270929 A1 | 11/2006 | Bouma et al. | |
| 2007/0238955 A1 | 10/2007 | Tearney et al. | |
| 2009/0118622 A1 | 5/2009 | Durkin et al. | |
| 2009/0137952 A1 | 5/2009 | Ramamurthy et al. | |
| 2009/0208143 A1 | 8/2009 | Yoon et al. | |
| 2009/0259102 A1 | 10/2009 | Koninckx et al. | |
| 2009/0296980 A1 * | 12/2009 | Yi | G06K 9/20 382/100 |
| 2010/0141829 A1 | 6/2010 | Jalali et al. | |
| 2010/0160904 A1 | 6/2010 | McMillan et al. | |
| 2011/0026037 A1 | 2/2011 | Forster et al. | |
| 2011/0057930 A1 | 3/2011 | Keller et al. | |
| 2011/0205552 A1 | 8/2011 | Bendall et al. | |
| 2011/0242285 A1 | 10/2011 | Byren | |
| 2011/0273548 A1 | 11/2011 | Uchiyama et al. | |
| 2012/0029829 A1 | 2/2012 | Li et al. | |
| 2012/0035434 A1 | 2/2012 | Ferren et al. | |
| 2012/0059224 A1 * | 3/2012 | Wellen | A61B 1/2275 600/200 |
| 2012/0177283 A1 * | 7/2012 | Wang | G06T 17/00 382/154 |
| 2012/0212595 A1 | 8/2012 | Parmar et al. | |
| 2013/0044185 A1 | 2/2013 | Krishnaswamy et al. | |
| 2013/0237754 A1 * | 9/2013 | Berglund | A61B 1/227 600/109 |
| 2014/0012141 A1 * | 1/2014 | Kim | A61B 1/00048 600/476 |
| 2014/0063204 A1 | 3/2014 | Siercks | |
| 2014/0085421 A1 | 3/2014 | Kuth et al. | |
| 2014/0171743 A1 * | 6/2014 | Heine | A61B 1/00142 600/200 |
| 2014/0240464 A1 | 8/2014 | Lee | |
| 2014/0375784 A1 | 12/2014 | Massetti | |
| 2015/0049331 A1 | 2/2015 | Ri | |
| 2015/0097968 A1 * | 4/2015 | Bergman | H04N 17/002 348/175 |
| 2015/0098636 A1 * | 4/2015 | Bergman | G06K 9/00201 382/128 |
| 2016/0374546 A1 * | 12/2016 | Berbee | A61B 1/227 600/109 |
| 2017/0027448 A1 * | 2/2017 | Carr | A61B 5/0086 |
| 2017/0041576 A1 * | 2/2017 | Kobayashi | H04N 9/097 |
| 2017/0071509 A1 * | 3/2017 | Pandey | A61B 5/12 |
| 2017/0195809 A1 | 7/2017 | Teran et al. | |
| 2018/0000336 A1 * | 1/2018 | Gilad-Gilor | A61B 1/00071 |
| 2018/0125345 A1 * | 5/2018 | Rebella | A61B 1/00082 |
| 2018/0156599 A1 * | 6/2018 | Boppart | G01B 9/02091 |
| 2018/0168440 A1 * | 6/2018 | Das | A61B 5/6817 |
| 2019/0038135 A1 * | 2/2019 | Lee | A61B 1/227 |

FOREIGN PATENT DOCUMENTS

| | | |
|---|---|---|
| CN | 102725688 A | 10/2012 |
| CN | 202714941 U | 2/2013 |
| CN | 102575928 B | 5/2015 |
| JP | 2003529432 A | 10/2003 |
| JP | 2008173397 A | 7/2008 |
| JP | 2009273655 A | 11/2009 |
| JP | 2010179021 A | 8/2010 |
| WO | 2001076452 A2 | 10/2001 |
| WO | 2010143692 A1 | 12/2010 |

(56) References Cited

FOREIGN PATENT DOCUMENTS

| WO | 2011027127 A2 | 3/2011 |
|---|---|---|
| WO | 2011120526 A1 | 10/2011 |
| WO | 2012059253 A1 | 5/2012 |

OTHER PUBLICATIONS

Barrera, F., et al., "Optical and Spectroscopic Properties of Human Whole Blood and Plasma with and without Y2O3 and Nd3+:Y2O3 Nanoparticles," Lasers Med Sci, 8 pages (Feb. 2013).
Cardiac Procedures and Surgeries At-A-Glance, American Heart Association/American Stroke Association, 4 pages, 2012.
Eagle Eye Platinum RX Digital IVUS Catheter, Volcano Precision Guided Therapy, product brochure, printed 2012, 4 pages.
Evans, J.L., et al., Accurate Three-Dimensional Reconstruction of Intravascular Ultrasound Data, Circulation (American Heart Association, Inc.), 93, pp. 567-576 (1996).
GN Store Nord, "GN Store Nord Invests $12 Million in Ear Scanning Company," hearingreview.com (2012).
Goodwin, J., A Capsule Camera Instead of a Colonoscopy, Health, May 10, 2011, 2 pages.
Gorthi, S.S., et al., Fringe Projection Techniques: Whither we are? Optics and Lasers in Engineering, 48(2), pp. 133-140 (2010).
Grundfest, W., et al., "Real-Time Percutaneous Optical Imaging of Anatomical Structures in the Heart Through Blood Using a Catheter-Based Infrared Imaging System," Seminars in Thoracic and Cardiovascular Surgery, 19:336-341 (2007).
Honda, Y., et al., "Frontiers in Intravascular Imaging Technologies," Circulation, 117:2024-2037 (2008).
IVUS Imaging Products Overview, Volcano Precision Guided Therapy, www.volcanocorp.com/products/ivus-imaging, 2012, 1 page.
Knight, B., et al., "Direct Imaging of Transvenous Radiofrequency Cardiac Ablation Using a Steerable Fiberoptic Infrared Endoscope," Heart Rhythm, 2:1116-21 (2005).
Logozzo, S., et al., "Recent Advances in Dental Optics—Part I: 3D Intraoral Scanners for Restorative Dentistry," Optics and Lasers in Engineering, 54:203-221 (2014).
Lundqvist, C.B., et al., "The Use of Imaging for Electrophysiological and Devices Procedures: A Report from the First European Heart Rhythm Association Policy Conference, Jointly Organized with the European Association of Cardiovascular Imaging (EACVI), the Council of Cardiovascular Imaging and the European Society of Cardiac Radiology," Europace, 15:927-936 (2013).
Maier-Hein et al., "Optical Techniques for 3D Surface Reconstruction in Computer-Assisted Laparoscopic Surgery," Medical Image Analysis 17, pp. 974-996, available May 3, 2013 (2013) (online <URL: http://isit.u-clermont1.fr/~ab/Publications/Maier-Hein_etal_MIA13.pdf>).
Mozaffarian, D., et al., "Heart Disease and Stroke Statistics—2015 Update: A Report from the American Heart Association," Circulation, 131:e29-e322, e535 (2014).
Roger, V., et al., "Heart Disease and Stroke Statistics—2012 Update: A Report from the American Heart Association," Circulation, 125:e2-e220, e1002 (2011).
Roggan, A., et al., "Optical Properties of Circulating Human Blood," Part of the SPIE Conference on Optical Diagnostics of Biological Fluids III, SPIE vol. 3252, pp. 70-82 (1998).
Takeda, M., et al., Fourier Transform Profilometry for the Automatic Measurement of 3-D Object Shapes, Applied Optics, vol. 22, No. 24, pp. 3977-3982 (Dec. 1983).
Toennies et al., "Swallowable Medical Devices for Diagnosis and Surgery: the State of the Art," Proc. IMechE vol. 224 Part C: J. Mechanical Engineering Science, pp. 1397-1414, Dec. 9, 2009 (2009) (online <URL: https://www.iris.sssup.it/retrieve/handle/11382/304585/994/JMESToennis_Webster.pdf>).
International Search Report and Written Opinion in PCT/US2018/017839, 13 pages, dated Apr. 11, 2018.

* cited by examiner

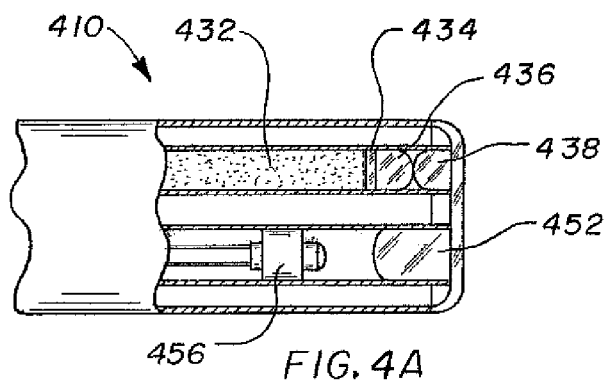
FIG. 4A
FIG. 4B
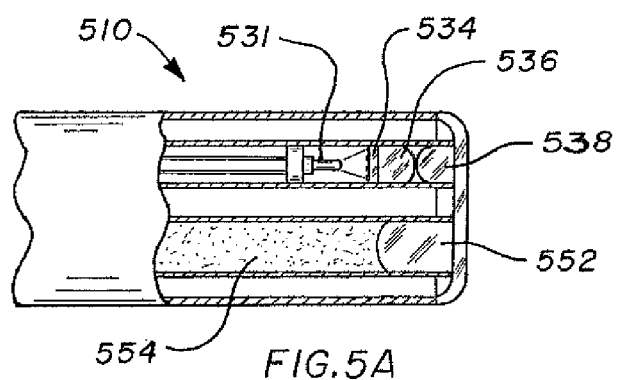
FIG. 5A
FIG. 5B
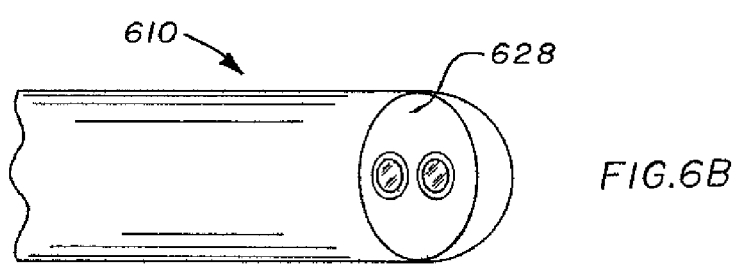
FIG. 6B
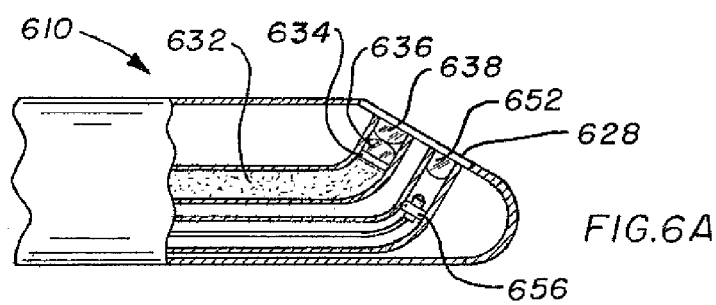
FIG. 6A

EAR CANAL MODELING USING PATTERN PROJECTION

CROSS-REFERENCE TO RELATED APPLICATIONS

This application claims the benefit of U.S. Provisional Application No. 62/458,691, filed Feb. 14, 2017, which is incorporated herein by reference in its entirety.

FIELD OF THE INVENTION

This disclosure relates generally to modeling of an ear canal, for example for fitting a hearing aid device to an ear canal.

BACKGROUND OF THE INVENTION

Hearing aids are commonly used to assist hearing-impaired persons, enabling them to hear sounds that they otherwise would not be able to hear. Many different types of hearing aids are available. Many hearing aids are designed such that all or part of the hearing aid fits in the outer ear cavity and/or inside the ear canal.

In order to get a good fit of the hearing aid, hearing aids are commonly custom made. Typically, an impression is made of the patient's outer ear cavity and/or ear canal, depending on the type of hearing aid desired. The impression is made by filling the desired area of the outer ear and/or ear canal with a quick-setting material, often a silicone material, allowing the material to set by curing in the ear. Once set, the impression is withdrawn, and an earmold for the hearing aid is made based on the impression.

The impression process has a number of potential drawbacks. For example, the process can be time-consuming, can cause patient discomfort, can cause patient anxiety, and can be expensive. The impression process can also cause damage to the ear and may not be suitable for measurements far into the ear canal and/or to the eardrum. The impression can be inaccurate, leading to a poor-fitting earmold. If the impression is of poor quality, the process may need to be repeated. In addition, the ear canal is typically dynamic, having different shapes depending on different jaw positions. This can be particularly problematic with patients with large temporomandibular (TMJ) joint movement that can affect the ear canal. It can be difficult and time-consuming to take multiple impressions, each representing a different jaw position.

A need exists for an improved system and method for modeling an ear canal.

SUMMARY OF THE INVENTION

The disclosure provides various systems and methods for making a three-dimensional model of the inside of an ear canal. Such a model is useful, for example, for manufacturing an earmold, such as for a hearing aid, to fit inside the ear canal.

One example of a system comprises an instrument having a probe adapted to be inserted into the ear canal. The probe comprises a narrow portion adapted to fit inside the ear canal and a wide portion adapted to be wider than the ear canal, the wide portion acting as a stop to limit the distance of the narrow portion of the probe into the ear canal. The narrow portion of the probe carries at least the distal end of an illumination subsystem and the distal end of an imaging subsystem. The wide portion of the probe may be formed by a tapered stop that is narrower at an end facing the ear canal and wider at an end facing away from the ear canal.

The illumination subsystem comprises a light source, a pattern screen, and a lens, with at least the lens being located in a distal end of the probe. The illumination subsystem is adapted to project light from the light source, through the pattern screen, and through the lens in order to project a pattern of light from the distal end of the probe onto a surface of the ear canal, the pattern being modulated by the three-dimensional surface of the ear canal. The imaging subsystem comprises a video camera and a lens, with at least the lens being located in the distal end of the probe. The imaging subsystem is adapted to capture in succession, at a video frame rate of the video camera, a plurality of individual images of the pattern of light projected onto the surface of the ear canal, each individual image corresponding to a video frame.

An example system may also comprise a computer subsystem adapted to calculate an individual digital three-dimensional representation from each individual image in the plurality of individual images. The computer subsystem may use a spatial signal modulation algorithm to perform the calculations. The calculations result in a plurality of individual digital three-dimensional representations of the imaged surface. The computer subsystem is also adapted to stitch together the individual digital three-dimensional representations to generate a digital three-dimensional model of the ear canal.

In one example, the illumination subsystem projects light only in a range of 10 nm to 550 nm. Alternatively, the illumination subsystem may project only green light, only blue light, or only ultraviolet light. The pattern screen may comprise a grating of alternating opaque and transparent stripes. The lens of the imaging subsystem may be a wide-angle lens that enables the video camera to capture in one image up to a full 180-degree view of the ear canal.

In an example method of making a three-dimensional model of the inside of an ear canal, the method comprises: inserting a probe into the ear canal, the probe carrying at least a distal end of an illumination subsystem and at least a distal end of an imaging subsystem; projecting light from the light source, through the pattern screen, and through the lens of the illumination subsystem, and thereby projecting a pattern of light from the distal end of the probe onto a surface of the ear canal, the pattern being modulated by the three-dimensional surface of the ear canal; capturing in succession, at a video frame rate of the video camera, a plurality of individual images of the pattern of light projected onto the surface of the ear canal, each individual image corresponding to a video frame; and calculating an individual digital three-dimensional representation from each individual image in the plurality of individual images, the calculations resulting in a plurality of individual digital three-dimensional representations, and stitching together the individual digital three-dimensional representations to generate a digital three-dimensional model of the ear canal.

BRIEF DESCRIPTION OF THE DRAWINGS

FIG. 4A shows another example of a distal end of an instrument, showing the distal tip of a probe in a partial cut-away view.

FIG. 4B shows an end view of the distal tip of the probe of FIG. 4A.

FIG. 5A shows another example of a distal end of an instrument, showing the distal tip of a probe in a partial cut-away view.

FIG. 5B shows an end view of the distal tip of the probe of FIG. 5A.

FIG. 6A shows another example of a distal end of an instrument, showing the distal tip of a probe in a partial cut-away view.

FIG. 6B shows a top view of the distal tip of the probe of FIG. 6A.

DETAILED DESCRIPTION

Figure 1:
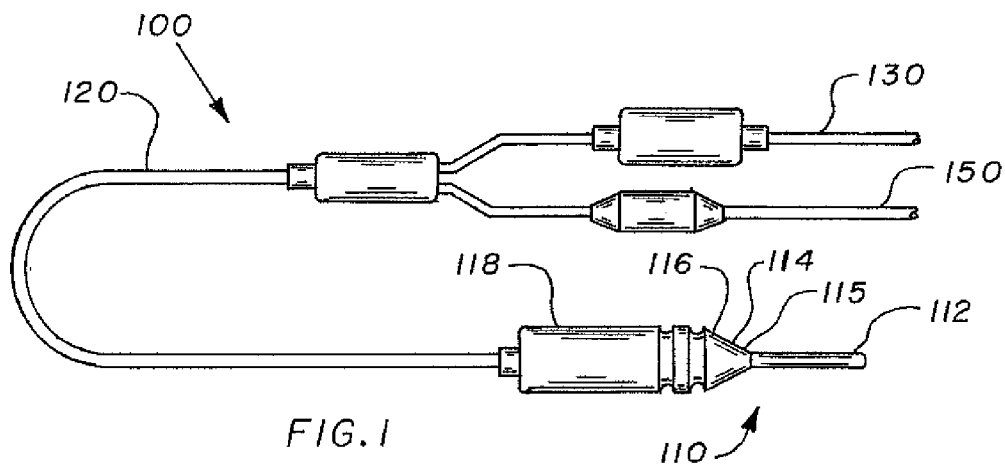
FIG. 1 illustrates an instrument that is a component of a system for generating a three-dimensional model of an ear canal.

In an example, a system for making an earmold for a hearing aid comprises a system for generating a three-dimensional model of an ear canal of a human or animal patient and a system for manufacturing an earmold using that three-dimensional model. The system for generating the three-dimensional model of the ear canal uses spatial signal modulation (SSM) to determine the dimensions of the ear canal for anatomical surface modeling. The spatial signal modulation apparatus may utilize projection and image-capturing optics co-located at the distal tip of a probe. The model of the ear canal may be a model of all or only a portion of the ear canal, and it may include modeling of all or part of the eardrum (tympanic membrane) and/or all or part of the outer ear.

In this example, a system for generating the three-dimensional model of the ear canal comprises a probe, an illumination subsystem for projecting a light pattern onto the surface of the ear canal, and an imaging subsystem for capturing a series of individual images, each individual image being an image of a part the ear canal surface with the light pattern projected onto it, the light pattern being deformed or modulated by the contours of the surface. The system for generating the three-dimensional model of the ear canal further comprises a computer subsystem running software comprising a spatial signal modulation algorithm for converting each individual image in the series of images into an individual digital point cloud, each individual digital point cloud representing a three-dimensional model of a part the ear canal surface, and a stitching algorithm for stitching together the individual digital point clouds into an overall digital point cloud, the overall digital point cloud representing a three-dimensional model of the ear canal.

A system for manufacturing an earmold using the three-dimensional model of the ear canal may comprise a three-dimensional printer that prints the earmold based upon the three-dimensional model of the ear canal. In an alternative, a system for manufacturing an earmold using the three-dimensional model of the ear canal may comprise a three-dimensional printer that prints a mold for making the earmold based upon the three-dimensional model of the ear canal. Then the earmold is molded from that printed mold. In another alternative, a system for manufacturing an earmold using the three-dimensional model of the ear canal may comprise a three-dimensional printer that prints a part in the shape of the desired earmold based upon the three-dimensional model of the ear canal. Then, the printed part is used to make a mold for the earmold, and the earmold is molded from that mold. Alternatively, the earmold is thermoformed using the printed part. In another alternative, a system for manufacturing an earmold using the three-dimensional model of the ear canal may comprise machining or otherwise manufacturing a mold based upon the three-dimensional model of the ear canal and then molding the earmold using that mold.

In an example system for generating the three-dimensional model of the ear canal, the probe is adapted to allow a distal tip of the probe to be inserted into the ear canal and moved therein in order to obtain the series of images. The probe generally has a narrow portion that can fit inside the ear canal and a wide portion that cannot fit inside the ear canal. The probe may include a tapered stop that is narrower at one end than the other end. In such a case, the narrow portion of the probe may be a tube connected to the narrower end of the tapered stop and/or the narrower end of the tapered stop itself, and the wide portion of the probe may be the wider end of the tapered stop and/or a part connected to the wider end of the tapered stop. The tapered stop can have any suitable shape gradually transitioning from a narrower end to a wider end, for example conical, frustoconical, or curved or parabolic versions of such shapes. The wide portion of the probe acts as a stop that prevents the narrow portion of the probe from being inserted too far into the ear canal, so as to prevent damage to the eardrum or other injury.

FIG. 1 illustrates an instrument 100 that is a component of a system for generating a three-dimensional model of the ear canal. The instrument 100 carries projection and imaging optics for distal projection and image capture. The instrument 100 comprises a probe 110 at its distal end. The probe 110 has a narrow portion in the form of a rigid or semi-rigid tube 112 at its distal end. The probe 110 include a tapered stop 114 that is narrower at one end 115 than the other end 116. The tube 112 is connected to the narrower end 115 of the tapered stop 114. The wider end 116 of the tapered stop 114 forms the wide portion of the probe 110. The wider end 116 is connected to generally cylindrical portion 118, which can act as a grip or handle. The tapered stop 114 is oriented so that its narrower end 115 faces the tube 112 and thus faces toward the ear. The narrow portion or tube 112 can fit inside the ear canal, while the wide portion or wider end 116 of the tapered stop 114 cannot fit inside the ear canal. Thus, the wide portion of the probe, and in particular the wider end 116 of the tapered stop 114, acts as a stop that prevents the narrow portion of the probe from being inserted too far into the ear canal, so as to prevent damage to the eardrum or other injury. The grip or handle 118 may have one or more grip features, such as one or more grooves or notches or indents, to facilitate handling and manipulation of the probe. A user can hold the grip or handle 118 of the probe and maneuver the tube 112 of the probe within and around the ear canal to get multiple ear canal views, as described below.

The instrument 100 further comprises a flexible tube 120, an illumination subsystem branch 130, and an imaging subsystem branch 150. The instrument 100 houses components of the illumination subsystem and the imaging subsystem.

Figure 2A:
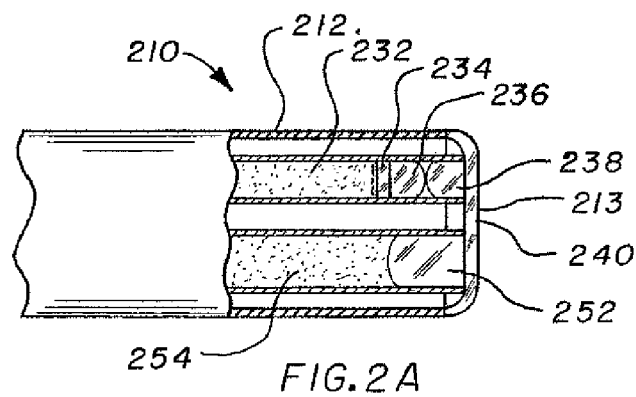
FIG. 2A shows an example of a distal end of an instrument, showing the distal tip of a probe in a partial cut-away view.
Figure 2B:
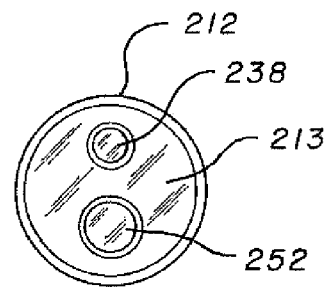
FIG. 2B shows an end view of the distal tip of the probe of FIG. 2A.

FIG. 2A shows an example of a distal end of an instrument, showing the distal tip of a probe 210 in a partial cut-away view. FIG. 2B shows an end view of the distal tip of the probe 210. In this example, the illumination subsystem comprises a light source (not shown) at the proximal end of the instrument, an optical fiber 232, which may be a single optical fiber (with a solid core) or a bundle of optical fibers (which may be randomized or coherent), a pattern screen 234, a first lens 236, and a second lens 238. The optical fiber(s) 232 extends the length of the instrument from the light source to the components at the distal end of the instrument. When the light source is turned on, light travels from the light source, through the optical fiber(s) 232, through the pattern screen 234, through the lenses 236, 238, and is projected out of the distal end 240 of the probe.

The pattern screen 234 is a component that comprises or has on it a pattern of transparent and opaque areas. In one form, the pattern is a Ronchi grating of alternating opaque and transparent stripes. The spacing of the alternating stripes may be any suitable spacing, such as 10, 20, 30, 40, 50, or 60 opaque stripe pairs, or cycles, per millimeter. The pattern screen may be a sheet or thin plate of transparent material with the pattern printed, etched, deposited, or otherwise formed in it or on it. In one example, the pattern screen may be a thin plate of glass or mylar film with a pattern formed by vapor deposition of a chrome material or other suitable material. In the illustrated example, the pattern screen 234 has a grating on the side that faces the optical fiber(s) 232. The pattern screen 234 blocks the light in a pattern, so that the light exiting the pattern screen 234 is in that pattern. In this way, a light pattern is projected onto the target surface, which in this case is the surface of the ear canal. The three-dimensional contours of the target surface distort or modulate the projected light pattern in a way that provides information that is used by the system for three-dimensional calculations. For example, in the case of a grating such as a Ronchi grating, the grating is projected onto the target surface, with the alternating stripes distorted or modulated due to the contours of the surface.

The pattern screen is a fixed component. The pattern screen does not move within the instrument, and the pattern of the pattern screen is fixed, i.e., it is constant and does not change.

The lenses 236, 238 are designed for projecting the pattern of light from the pattern screen 234 onto the target surface. One or more lenses may be used. In this example, lens 236 has a flat surface at its proximal side and a convex surface at its distal side, and lens 238 has a convex surface at its proximal side and a flat surface at its distal side. The flat surface of lens 236 is adjacent to and abuts the pattern screen 234, while the convex surface of lens 236 is adjacent to and abuts the convex surface of lens 238. The flat surface of lens 238 faces outwardly from the distal end 240 of the probe. The lenses may be of the single or multiple element type with flat, spherical, aspherical, convex, or concave surfaces, or gradient index rod lenses (GRIN) capable of producing the desired field of view (FOV). Short or zero length back focus distances may be utilized to maximize light transmission through the pattern screen from the fiber and focus the image of the pattern to be projected. Fields of view (FOV) of up to 180-degrees are possible with FOV in the range of 90-degrees more readily available and with reduced edge aberrations. The lens(es) may be designed to project the light pattern onto the target surface in a defocused manner. For example, a pattern of alternating stripes of light may be defocused to form a sinusoidal pattern on the target surface. In an alternative, the lens(es) may be designed to project the light pattern onto the target surface in a focused manner.

The light source may be any suitable light source, including but not limited to laser light, halogen light, LED light, and/or incandescent light. As one example, a broad spectrum visible light source may be used, projecting white light. As another example, a single wavelength or narrow band of wavelengths of light may be projected.

The wavelength (or frequency) may tuned to the medium and surface being measured. The ear canal can present a moist environment, causing specular reflections and/or absorption of some wavelengths of light. The specular reflections and absorption of light by the skin cells can be moderated by proper selection of the wavelength of the carrier light. In the case of the ear canal, projecting a spatial signal through a gaseous media (air) onto epithelial cells, shorter wavelengths (green or blue to ultraviolet) can help to reduce or eliminate the effects of both specular reflections and absorption of light by the skin cells. Thus, for imaging in the ear canal, through air onto the skin surface of the ear canal, a shorter wavelength light may be advantageous, such as green light, blue light, violet light, and/or ultraviolet light. For imaging in the ear canal, light in a wavelength range of 10 nm to 550 nm may be advantageous; in particular, light in a wavelength range of 490 nm to 550 nm, 465 nm to 490 nm, 400 nm to 465 nm, and/or 10 nm to 400 nm (ultraviolet) may be advantageous.

In the example of FIGS. 2A and 2B, the imaging subsystem comprises a lens 252, an optical fiber bundle 254, and an image sensor or digital video camera (not shown) located at the proximal end of the instrument. The camera may be, for example, a CCD camera or a CMOS camera. In one example, the camera is a 1.3 million pixel CCD monochrome camera. Cameras with higher or lower resolutions may be used. The optical fiber bundle 254 is a coherent imaging optical fiber bundle that extends from the distal end of the instrument adjacent to the lens 252 to the digital video camera at the proximal end of the instrument in order the enable the digital video camera to capture digital images of the target surface. The lens 252 may have a convex surface facing the optical fiber bundle 254 and a flat surface facing outwardly from the distal end 240 of the probe. The lens 252 may be a wide-angle lens that enables the camera to capture in one image a full cross-section or up to a 180-degree view of the ear canal. Similar to the projection optics, the imaging lenses may be of the single or multiple element type with flat, spherical, aspherical, convex, or concave surfaces, or gradient index rod lenses (GRIN) capable of producing the desired FOV.

As the probe is moved to different views in the ear canal, the camera captures successive images of the light pattern that is projected on and modulated by the ear canal surface. The camera captures an image with each frame of the video. In the United States video cameras generally follow the National Television System Committee (NTSC) standard of 30 frames per second, while Europe and Asia follow the Phase Alternating Line (PAL) standard of 25 frames per second. Specialized video cameras with higher frame rates are available that enable more frames to be captured in a given time to better cover rapidly changing scenes or moving objects. Thus, the imaging subsystem is adapted for capturing a series of individual images, each individual image being an image of a part the ear canal surface with the light pattern projected onto it, the light pattern being deformed or modulated by the contours of the ear canal surface.

The distal components of the illumination subsystem (in this embodiment, the distal end of optical fiber(s) 232, the pattern screen 234, and the lenses 236, 238) and the distal components of the imaging subsystem (in this embodiment, the distal end of optical fiber bundle 254 and the lens 252) are housed within the probe 210. The probe 210 has a housing in the form of a tube 212, which in this example is a cylindrical tube, although other shapes are possible. The end of the probe 210 is covered by an end cap 213, with access areas (holes or transparent areas) for the lenses of the illumination and imaging subsystems.

Figure 3A:
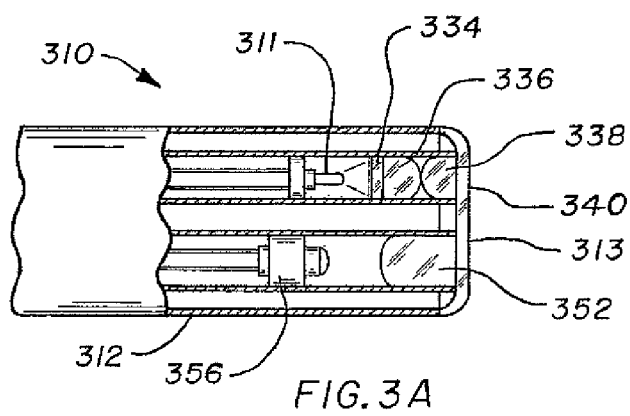
FIG. 3A shows another example of a distal end of an instrument, showing the distal tip of a probe in a partial cut-away view.
Figure 3B:
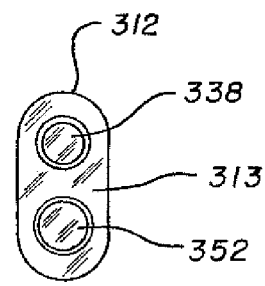
FIG. 3B shows an end view of the distal tip of the probe of FIG. 3A.

FIG. 3A shows another example of a distal end of an instrument, showing the distal tip of a probe 310 in a partial cut-away view. FIG. 3B shows an end view of the distal tip of the probe 310. In this example, the illumination subsystem comprises a light source 311 at the distal end of the instrument. Wiring for operation of the light source extends through the instrument and connects the light source to a power source. The illumination subsystem further comprises a pattern screen 334, a first lens 336, and a second lens 338, which may be similar to the pattern screen 234 and lenses 236, 238. When the light source 311 is turned on, light travels from the light source 311 through the pattern screen 334, through the lenses 336, 338, and is projected out of the distal end 340 of the probe. The light source, wavelength(s), and projected pattern may be similar in structure and function to those described above.

In FIGS. 3A and 3B, the imaging subsystem comprises a camera 356 at the distal end of the instrument (at the distal end of the probe), along with a lens 352. Placing the camera 356 at the distal end of the instrument and at the distal end of the probe can enable capturing of higher resolution images, since the coherent fiber optic bundle, which can limit resolution, may not be needed as part of the imaging subsystem in such an embodiment. The imaging subsystem operates in a similar manner as the imaging subsystem in FIGS. 2A and 2B. As the probe is moved to different views in the ear canal, the camera captures successive images of the light pattern that is projected on and modulated by the ear canal surface, capturing an image with each frame of video.

As with the embodiment of FIGS. 2A-2B, in the embodiment of FIGS. 3A-3B the distal components of the illumination subsystem (in this embodiment, the light source 311, the pattern screen 334, and the lenses 336, 338) and the distal components of the imaging subsystem (in this embodiment, the camera 356 and the lens 352) are housed within the probe 310. The probe 310 has a housing in the form of a tube 312, which in this example is has a cross-sectional shape in the form of a rectangle with semi-circles at opposite ends. Other shapes are possible, such as oval, rectangular with rounded corners, square with rounded corners, etc. The end of the probe 310 is covered by an end cap 313, with access areas (holes or transparent areas) for the lenses of the illumination and imaging subsystems.

FIG. 4A shows another example of a distal end of an instrument, showing the distal tip of a probe 410 in a partial cut-away view. FIG. 4B shows an end view of the distal tip of the probe 410. In this example, the illumination subsystem is similar in structure and function to that described above with respect to FIGS. 2A and 2B, and the imaging subsystem is similar in structure and function to that described above with respect to FIGS. 3A and 3B. The illumination subsystem comprises a light source (not shown) at the proximal end of the instrument, an optical fiber 432, a pattern screen 434, a first lens 436, and a second lens 438, similar in structure and function to the light source, optical fiber 232, pattern screen 234, first lens 236, and second lens 238 described above with respect to FIGS. 2A and 2B. The imaging subsystem comprises a lens 452 and a camera 456 at the distal end of the instrument, similar in structure and function to the lens 352 and camera 356 described above with respect to FIGS. 3A and 3B.

FIG. 5A shows another example of a distal end of an instrument, showing the distal tip of a probe 510 in a partial cut-away view. FIG. 5B shows an end view of the distal tip of the probe 510. In this example, the illumination subsystem is similar in structure and function to that described above with respect to FIGS. 3A and 3B, and the imaging subsystem is similar in structure and function to that described above with respect to FIGS. 2A and 2B. The illumination subsystem comprises a light source 531 at the distal end of the instrument, a pattern screen 534, a first lens 536, and a second lens 538, similar in structure and function to the light source 311, pattern screen 334, first lens 336, and second lens 338 described above with respect to FIGS. 3A and 3B. The imaging subsystem comprises a lens 552, an optical fiber bundle 554, and a camera (not shown) located at the proximal end of the instrument, similar in structure and function to the lens 252, optical fiber bundle 254, and camera described above with respect to FIGS. 2A and 2B.

FIG. 6A shows another example of a distal end of an instrument, showing the distal tip of a probe 610 in a partial cut-away view. FIG. 6B shows a top view of the distal tip of the probe 610. The instrument has illumination and imaging subsystems that are similar in structure and function to that described above with respect to FIGS. 4A and 4B. The illumination subsystem comprises a light source (not shown) at the proximal end of the instrument, an optical fiber 632, a pattern screen 634, a first lens 636, and a second lens 638, similar in structure and function to the light source, optical fiber 232, pattern screen 234, first lens 236, and second lens 238 described above with respect to FIGS. 2A and 2B. The imaging subsystem comprises a lens 652 and a camera 656 at the distal end of the instrument, similar in structure and function to the lens 352 and camera 356 described above with respect to FIGS. 3A and 3B. In the examples of FIGS. 2A-2B, 3A-3B, 4A-4B, and 5A-5B, the direction of the projection of the pattern and the direction of the image capture are aligned with the longitudinal axis of the probe. The imaging optics face forward, making the probe "forward-looking". In the example of FIGS. 6A-6B, the distal tip of the probe is designed so that the projection of the pattern and the capturing of the images is done at an angle to the axis of the probe. The imaging optics face to the side, making the probe "side-looking". The distal tip of the tube of the probe has a surface 628 that is angled with respect to the axis of the probe, for example forming an angle of 30 degrees (or in the range of 10 degrees to 90 degrees) with the axis of the probe. The optical fiber(s) 632 has a bend near the distal end to direct the illumination optics including lens 238 normal to the angled surface 628 of the probe, so that an optical axis of the illumination optics is normal to the angled surface 628 of the probe. Similarly, the wiring for the camera 656 bends so that the camera 656 and lens 652 are directed normal to the angled surface 628 of the probe, so that an optical axis of the imaging optics is normal to the angled surface 628 of the probe. An orientation that directs the projection of the pattern and the capturing of the images at an angle with respect to the axis of the probe can help obtain images around the full ear canal. The user can maneuver the probe by turning it to face the projection optics and camera at different target surfaces around the ear canal.

Figure 7:
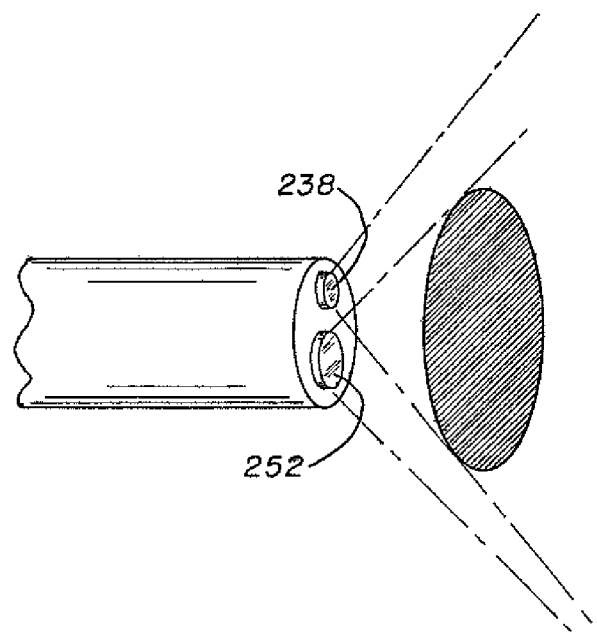
FIG. 7 schematically illustrates an area of overlap of a projected pattern and an area of image capture.

FIG. 7 schematically illustrates an area of overlap of a projected pattern and an area of image capture. The lens 238 of the projection optics may be a wide-angle lens to project the pattern over a wide area. Similarly, the lens 252 of the imaging optics may be a wide-angle lens that enables the camera to capture an image over a wide area. The area of overlap between the projected pattern and the captured image is shown. As stated above, the lens 252 may be a wide-angle lens that enables the camera to capture in one image a full cross-section or up to 180-degree view of the ear canal. Alternatively, it may capture a smaller area in one image, and the probe can be maneuvered as needed to image the entire desired ear canal area.

Figure 8:
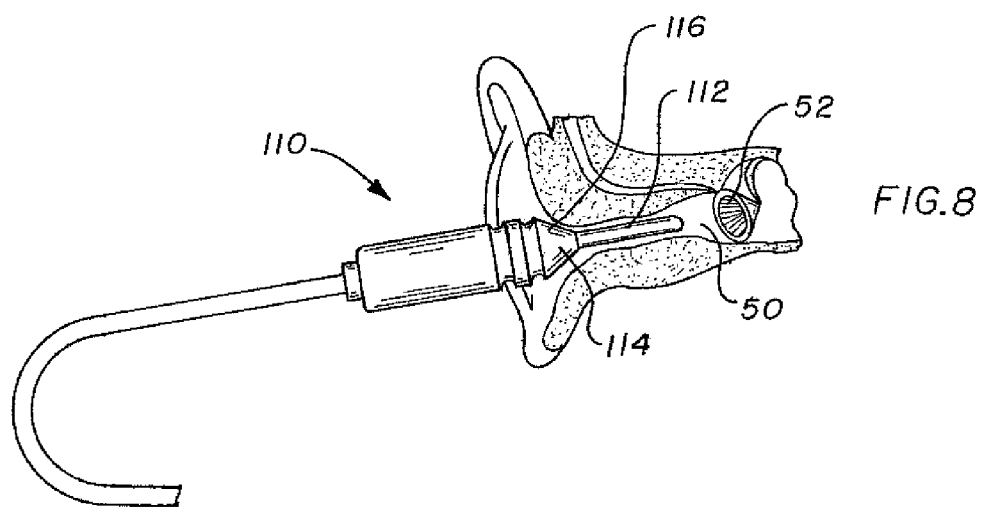
FIG. 8 shows use of the instrument of FIG. 1.

FIG. 8 shows use of an instrument comprising probe 110. The user holds the probe and maneuvers the distal tube 112 into the ear canal 50. The imaging subsystem is turned on, and with each frame the camera captures an image of the pattern projected onto the ear canal surface (including, if desired, the surface of the eardrum 52). The user maneuvers the tube 112 distally into the ear canal 50, and/or around the ear canal 50, while the camera captures successive images. The wide portion of the probe, and in particular the wider end 116 of the tapered stop 114, prevents the user from pushing the tube 112 too far into the ear canal 50, thereby protecting the eardrum 52.

Figure 9:
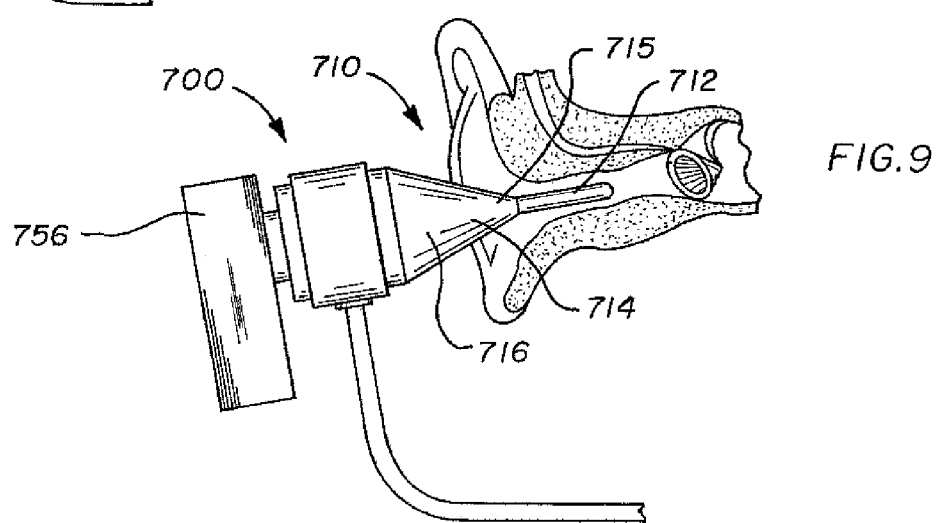
FIG. 9 shows an alternate instrument that is a component of a system for generating a three-dimensional model of an ear canal.

FIG. 9 shows an alternate instrument 700 that is a component of a system for generating a three-dimensional model of the ear canal. The instrument 700 comprises a probe 710 at its distal end. The probe 710 has a narrow portion in the form of a rigid or semi-rigid tube 712 at its distal end. The probe 710 include a tapered stop 714 that is narrower at one end 715 than the other end 716. The tube 712 is connected to the narrower end 715 of the tapered stop 714. The wider end 716 of the tapered stop 714 forms the wide portion of the probe 710. The tapered stop 714 is oriented so that its narrower end 715 faces the tube 712 and thus faces toward the ear. The narrow portion or tube 712 can fit inside the ear canal, while the wide portion or wider end 716 of the tapered stop 714 cannot fit inside the ear canal. Thus, the wide portion of the probe, and in particular the wider end 716 of the tapered stop 714, acts as a stop that prevents the narrow portion of the probe from being inserted too far into the ear canal, so as to prevent damage to the eardrum or other injury.

The instrument 700 carries a camera 756 that is part of the imaging subsystem. The imaging subsystem is similar to the imaging subsystem in FIGS. 2A-2B in that the camera is not located in the probe but rather is kept external to the ear, with a coherent fiber optic bundle connecting the camera to a lens at the distal end of the probe.

Figure 10:
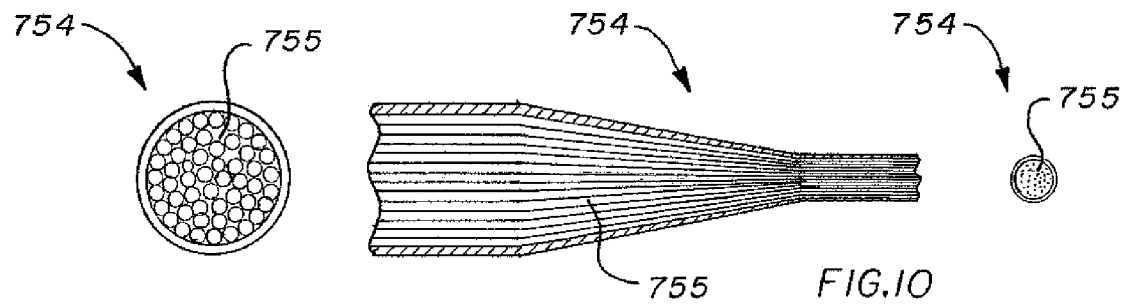
FIG. 10 shows an example of a fiber optic bundle that is usable with the instrument of FIG. 9.

FIG. 10 shows an example of a fiber optic bundle 754 that is usable with the instrument 700. The fiber optic bundle 754 comprises a plurality of individual optical fibers 755 arranged in a manner that preserves their relative orientation from the distal end of the probe to the camera. The fiber optic bundle 754 may be tapered such that a small profile at the distal end of the probe can be expanded to a larger viewing area for the camera 756. The camera 756 may have a display screen that displays in real time the surface of the ear canal. In this manner, the user (e.g., physician) can use the instrument as an otoscope for inspection of the ear in addition to using it to generate the three-dimensional model.

Similarly, in other embodiments, a display may be used, e.g., a display on the camera itself and/or an associated computer display or other display, in order to show in real time the view at the distal tip of the probe, for use of the instrument as an otoscope as well as for guidance in selecting areas for scanning and modeling.

Figure 11:
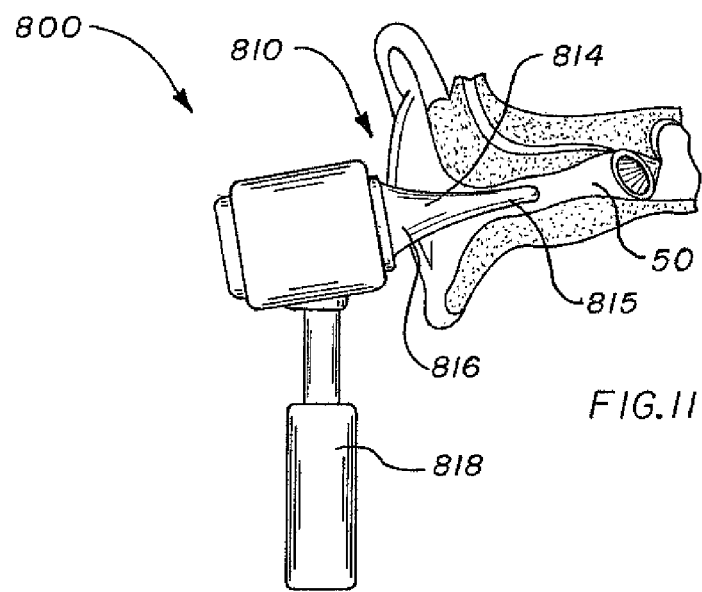
FIG. 11 shows another alternate instrument that is a component of a system for generating a three-dimensional model of an ear canal.

FIG. 11 shows another alternate instrument 800 that is a component of a system for generating a three-dimensional model of the ear canal. The instrument 800 comprises a probe 810 at its distal end. The probe 810 include a tapered stop 814 that is narrower at one end 815 than the other end 816. The narrower end 815 of the tapered stop 814 forms the narrow portion of the probe 810. The wider end 816 of the tapered stop 814 forms the wide portion of the probe 810. The tapered stop 814 is oriented so that its narrower end 815 faces toward the ear. The narrow portion or narrower end 815 of the tapered stop 814 can fit inside the ear canal 50, while the wide portion or wider end 816 of the tapered stop 814 cannot fit inside the ear canal. Thus, the wide portion of the probe, and in particular the wider end 816 of the tapered stop 814, acts as a stop that prevents the narrow portion of the probe from being inserted too far into the ear canal, so as to prevent damage to the eardrum or other injury. The instrument 800 has a handle 818 connected to the wider end 816 of the tapered stop. The handle 818 allows the user to maneuver the probe 810 within the ear canal to obtain the desired views (similar, for example, to handle 118).

In addition to the instruments and probes described above, and the illumination and imaging subsystems described above, a system for generating a three-dimensional model of an ear canal may further comprise a computer subsystem with one or more processors, memory, and software. The software comprises a spatial signal modulation algorithm for converting each individual image in the series of successive images from the video camera into an individual digital point cloud, each individual digital point cloud representing a three-dimensional model of a part the ear canal surface. The computer subsystem calculates an individual digital point cloud for each individual image.

In SSM, a 2-dimensional (2-d) signal with its intensity level varying across a distance (as opposed to varying over time as in radio signals), is generated by the pattern screen and projected through the lens(es) onto a 3-dimensional (3-d) target to be modeled. The 3-d shape of the target surface modulates, or changes, the signal which is then reflected back and imaged by the camera. Given prior knowledge of the original transmitted signal, the changes to the imaged reflection can be isolated and the continuous quantitative 3-d shape of the target surface can be calculated. There are many types of algorithms that may be employed to analyze the modulated spatial signals, including: moire interferometry, fringe projection, Fourier transform or deconvolution profilometry, and others. Image corrections may be used to account for aberrations caused by the optical system including: radial aberrations (commonly barrel or pincushion distortions), misalignment, or lens edge distortions. These can be corrected for during a one-time systemic calibration procedure which identifies and quantifies the unique optical effects in the system and determines the mathematical corrections to negate their influence. These aberration definitions can then be quickly applied to produce properly compensated images to be used for SSM 3-d modeling.

The computer subsystem can calculate an individual digital point cloud for each individual image from the camera at or faster than the frame rate of the camera. In this way, the display can show a display of the calculated three-dimensional surface being imaged in real time (e.g., at 25 frames per second, 30 frames per second, or faster, such as thousands of frames per second).

The software may further comprise a stitching algorithm for stitching together the individual digital point clouds into an overall digital point cloud, the overall digital point cloud representing a three-dimensional model of the ear canal. For example, each point cloud in a succession of frames changes from the previous point cloud due to the incremental movement occurring relative to the previous frame. The bulk of the point cloud data is identical to the one preceding it, but it includes the addition of a small portion that was not present in the previous frame due to a change in relative position during the small interframe time interval. Mathematical processing identifies these areas that have changed and adds, or stitches them, onto the overall 3-d model. Each successive frame causes another incremental addition to the model, eventually resulting in a single large continuous 3-d surface model of the entire volume under study. Each frame of surface data can be thought of as overlapping pieces of a mosaic representing the chamber into which the probe was inserted. The addition of data to each frame from an inertial navigation device would be beneficial by explicitly locating that frame in space, thereby assisting with model reconstruction or permitting closer inspection of details contained within that individual point cloud.

The following describes a method of using a system as described above to generate a three-dimensional model of an ear canal, and optionally to also manufacture an earmold, such as for a hearing aid, based upon that three-dimensional model of an ear canal. First, the user (e.g., physician) handles the instrument and maneuvers the distal tip of the probe into the ear canal. The illumination subsystem is activated, causing the light source to project light through the pattern screen, the patterned light passing through the lens(es) and being projected onto the target surface of the ear canal. The imaging subsystem is activated, and the camera continuously captures a series of successive individual images of the pattern as projected on and modulated by the target surface. The camera captures an individual image for each frame of video. The individual images in the series of successive individual images differ from each other due to relative movement between the probe and the surface being imaged. As the probe is moved, different images are captured. The user maneuvers the probe to obtain images of the entire surface that is desired to be modeled, including all or part of the ear canal and, if desired, the ear drum and/or all or part of the outer ear. The computer system and software comprising the spatial signal modulation algorithm uses each individual image in the series of images as input and, at or faster than frame rates, creates an individual digital point cloud, or three-dimensional map, for each individual image in the series of successive images. Each individual digital point cloud may be generated from the entire corresponding image or, if desired in order to eliminate edge distortion, from only a central portion of the corresponding image. For example, the central 70% to 80% of the image field may be used in order to minimize the effects of optical distortion near the lens boundaries. Each individual digital point cloud represents a three-dimensional model of a part the ear canal surface. By generating the digital point clouds at the frame rate of the camera, the systems enables a display to show in real time, at frame rates of the camera, a live and nearly instantaneous three-dimensional, full-field representation of the surface being viewed. The computer system and software comprising the stitching algorithm registers and stitches together the individual digital point clouds into an overall digital point cloud, the overall digital point cloud representing a three-dimensional model or map of the ear canal. Thus, the system performs continuous mapping at rapid frame rates, and it assembles the individual surface models into single continuous entity.

Using the three-dimensional model of the ear canal, a system for manufacturing an earmold may use a three-dimensional printer to print the earmold, or to print a mold in which the earmold is subsequently molded, or to print a part in the shape of the desired earmold, from which the earmold is then made by molding or thermoforming. In another alternative, a system for manufacturing an earmold using the three-dimensional model of the ear canal machines or otherwise manufactures a mold based upon the three-dimensional model of the ear canal and then molds the earmold using that mold.

A system as described herein has a number of advantages. The device generates highly accurate three-dimensional models, facilitating the manufacture of well-fitting earmolds. The device takes measurements quickly, thereby reducing the time needed from the user (physician) and patient. The device has a small and maneuverable profile, enabling measurements through the narrow and tortuous ear canal and deep into the ear canal, including measurements of the eardrum. The device's rapid measurements make it less susceptible to irregularities due to anatomical movement, which can be present in the ear canal because the pliable or semi-rigid tissue can change shape with patient movement, respiration, muscle contractions, jaw positions, etc. The device can quickly and easily make multiple models, such as of the same ear canal with the patient's jaw in different positions. The device does not have the discomfort of inserting an impression material into an ear and leaving it in place during curing. The device is reliable, with no moving parts, lessening potential for damage or breaking. The device may be used as an otoscope for ear inspection as well as for three-dimensional scanning and model generation. The device is easy to clean. The distal part of the probe may be provided with a disposable cover that can be discarded and replaced after each patient.

The embodiments described and illustrated herein are only examples, as many variations are possible. The materials, dimensions, components, order of steps, and operation may be varied without departing from the scope of the invention, which is limited only by the appended claims.

What is claimed is:

1. A system for making a three-dimensional model of the inside of an ear canal in order to manufacture an earmold to fit inside the ear canal, the system comprising:
   an instrument comprising a probe adapted to be inserted into the ear canal, the probe comprising a tapered stop that has a narrower end and a wider end, the narrower end sized to fit inside the ear canal, the wider end sized not to fit inside the ear canal, the wider end adapted to act as a stop that limits the distance of the probe into the ear canal;
   an illumination subsystem comprising a light source, a pattern screen, wherein the pattern screen comprises a pattern of transparent and opaque areas, and a lens, with at least the lens being located in a distal end of the probe, the illumination subsystem adapted to project light from the light source, through the pattern screen, and through the lens in order to project a pattern of light from the distal end of the probe onto a surface of the ear canal, the pattern being modulated by the surface of the ear canal; and an imaging subsystem comprising a video camera and a lens, with at least the lens being located in the distal end of the probe, the imaging subsystem adapted to capture in succession, at a video frame rate of the video camera, a plurality of individual images of the pattern of light projected onto the surface of the ear canal, each individual image corresponding to a video frame.

2. A system as recited in claim 1, wherein the probe further comprises a tube connected to the narrower end of the tapered stop.

3. A system as recited in claim 2, wherein the tube is rigid.

4. A system as recited in claim 1, wherein the probe further comprises a handle connected to the wider end of the tapered stop.

5. A system as recited in claim 1, wherein the illumination subsystem projects light only in a range of 10 nm to 550 nm.

6. A system as recited in claim 1, wherein the illumination subsystem projects only green or blue light.

7. A system as recited in claim 1, wherein the illumination subsystem projects only ultraviolet light.

8. A system for making a three-dimensional model of the inside of an ear canal in order to manufacture an earmold to fit inside the ear canal, the system comprising:
- an instrument comprising a probe adapted to be inserted into the ear canal;
- an illumination subsystem comprising a light source, a pattern screen, wherein the pattern screen comprises a pattern of transparent and opaque areas, and a lens, with at least the lens being located in a distal end of the probe, the illumination subsystem adapted to project light from the light source, through the pattern screen, and through the lens in order to project a pattern of light from the distal end of the probe onto a surface of the ear canal, the pattern being modulated by the surface of the ear canal; and
- an imaging subsystem comprising a video camera and a lens, with at least the lens being located in the distal end of the probe, the imaging subsystem adapted to capture in succession, at a video frame rate of the video camera, a plurality of individual images of the pattern of light projected onto the surface of the ear canal, each individual image corresponding to a video frame.

9. A method of making a three-dimensional model of the inside of an ear canal in order to manufacture an earmold to fit inside the ear canal, the method comprising:
- inserting a probe into the ear canal, the probe carrying at least a distal end of an illumination subsystem and at least a distal end of an imaging subsystem, the illumination subsystem comprising a light source, a pattern screen, wherein the pattern screen comprises a pattern of transparent and opaque areas, and a lens, with at least the lens being located in a distal end of the probe, the imaging subsystem comprising a video camera and a lens, with at least the lens being located in the distal end of the probe;
- projecting light from the light source, through the pattern screen, and through the lens of the illumination subsystem, and thereby projecting a pattern of light from the distal end of the probe onto a surface of the ear canal, the pattern being modulated by the surface of the ear canal; and
- capturing in succession, at a video frame rate of the video camera, a plurality of individual images of the pattern of light projected onto the surface of the ear canal, each individual image corresponding to a video frame.

10. A method as recited in claim 9, wherein the probe comprises a narrow portion adapted to fit inside the ear canal and a wide portion adapted to be wider than the ear canal, the wide portion acting as a stop to limit the distance of the probe into the ear canal.

11. A method as recited in claim 10, wherein the wide portion of the probe is part of a tapered stop that is narrower on a side facing the narrow portion of the probe.

12. A method as recited in claim 10, wherein the narrow portion of the probe is rigid.

13. A method as recited in claim 10, wherein the probe further comprises a handle connected to the wide portion of the probe.

14. A method as recited in claim 9, wherein the illumination subsystem projects light only in a range of 10 nm to 550 nm.

15. A method as recited in claim 9, wherein the illumination subsystem projects only green or blue light.

16. A method as recited in claim 9, wherein the illumination subsystem projects only ultraviolet light.

* * * * *